(12) United States Patent
Hafer et al.

(10) Patent No.: US 9,585,982 B1
(45) Date of Patent: Mar. 7, 2017

(54) SYSTEMS FOR DIFFUSING VOLATILE COMPOUNDS UTILIZING MOVEABLE PODS

(71) Applicant: The Dial Corporation, Scottsdale, AZ (US)

(72) Inventors: Kevin Hafer, Chandler, AZ (US); Keith Cardinal, Gilbert, AZ (US)

(73) Assignee: The Dial Corporation, Scottsdale, AZ (US)

( * ) Notice: Subject to any disclaimer, the term of this patent is extended or adjusted under 35 U.S.C. 154(b) by 0 days.

(21) Appl. No.: 14/982,890

(22) Filed: Dec. 29, 2015

(51) Int. Cl.
| A61L 9/04 | (2006.01) |
| A61L 9/12 | (2006.01) |
| A61L 9/01 | (2006.01) |
| A01M 1/20 | (2006.01) |

(52) U.S. Cl.
CPC ........... *A61L 9/125* (2013.01); *A01M 1/2055* (2013.01); *A61L 9/01* (2013.01); *A61L 9/048* (2013.01); *A61L 9/12* (2013.01)

(58) Field of Classification Search
CPC . A61L 9/01; A61L 9/125; A61L 9/048; A61L 9/12; A61L 9/04; A01M 1/2055
USPC .......................................... 239/6, 34, 57–60
See application file for complete search history.

(56) References Cited

U.S. PATENT DOCUMENTS

| 2,103,609 | A | * | 12/1937 | Bradburn | ............. | B60H 3/0007 |
| | | | | | | 239/59 |
| 2,642,310 | A | * | 6/1953 | Meek | ........................ | A61L 9/12 |
| | | | | | | 239/59 |
| 5,050,798 | A | | 9/1991 | Sullivan | | |
| 5,178,327 | A | | 1/1993 | Palamand et al. | | |
| 5,695,692 | A | | 12/1997 | Kennedy | | |
| 6,581,915 | B2 | | 6/2003 | Bartsch et al. | | |
| 6,834,847 | B2 | | 12/2004 | Bartsch et al. | | |
| 6,950,607 | B2 | | 9/2005 | Yip et al. | | |
| 7,011,795 | B2 | | 3/2006 | Thompson et al. | | |
| 7,734,159 | B2 | | 6/2010 | Beland et al. | | |
| 8,016,207 | B2 | | 9/2011 | Kvietok et al. | | |
| 8,170,405 | B2 | | 5/2012 | Harris | | |
| 8,385,730 | B2 | | 2/2013 | Bushman et al. | | |
| 8,483,553 | B2 | | 7/2013 | Tollens et al. | | |
| 2003/0175148 | A1 | | 9/2003 | Kvietok et al. | | |
| 2006/0081721 | A1 | | 4/2006 | Caserta et al. | | |
| 2009/0212124 | A1 | | 8/2009 | Kenny | | |

FOREIGN PATENT DOCUMENTS

| WO | 2004/105878 A1 | 12/2004 |
| WO | 2014/207273 A1 | 12/2014 |

* cited by examiner

*Primary Examiner* — Steven J Ganey
(74) *Attorney, Agent, or Firm* — P. Scott Smith

(57) ABSTRACT

A system for diffusing one or more volatile compounds included in a volatile compound mass includes a base and a pod tray, carried by the base. At least one pod is carried by the pod tray, the pod having a housing holding a volatile compound mass. The volatile compound mass and the housing are moveable relative to one another. An actuator is carried by the base, the actuator operable to engage the pod and move the housing and the volatile compound mass relative to one another. The pod and the actuator are positionable relative to one another such that the pod and the actuator can be positioned proximate to one another to enable the actuator to engage the pod and move the housing of the pod and the volatile compound mass relative to one another to thereby diffuse the volatile compound.

20 Claims, 4 Drawing Sheets

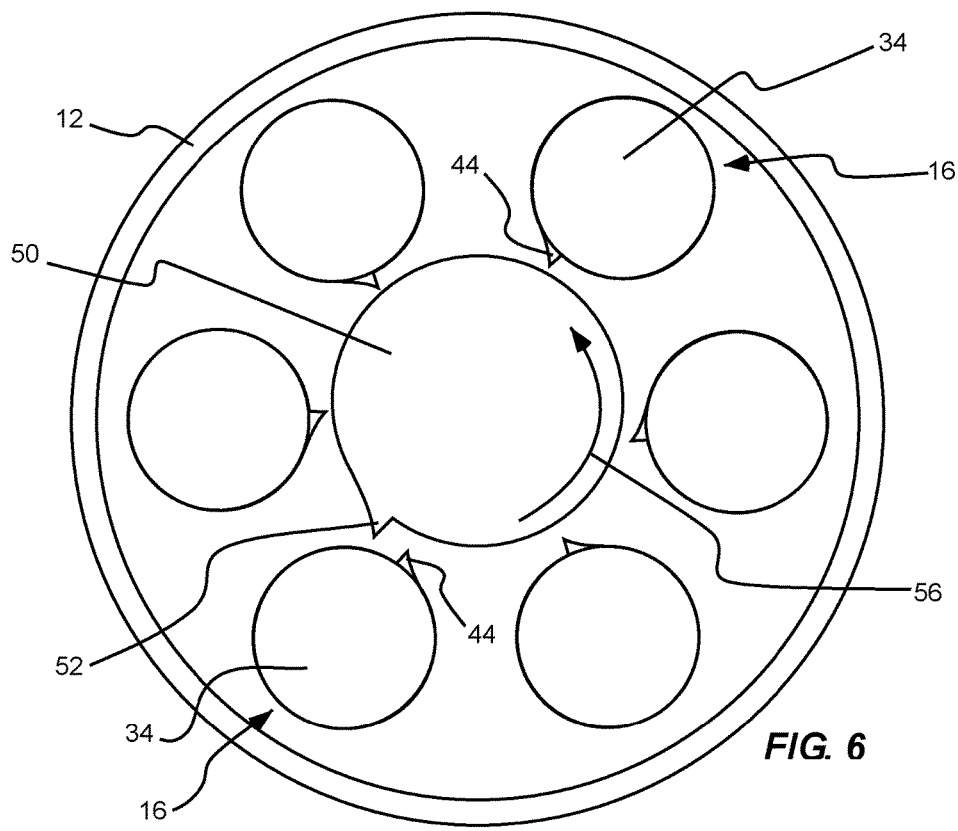
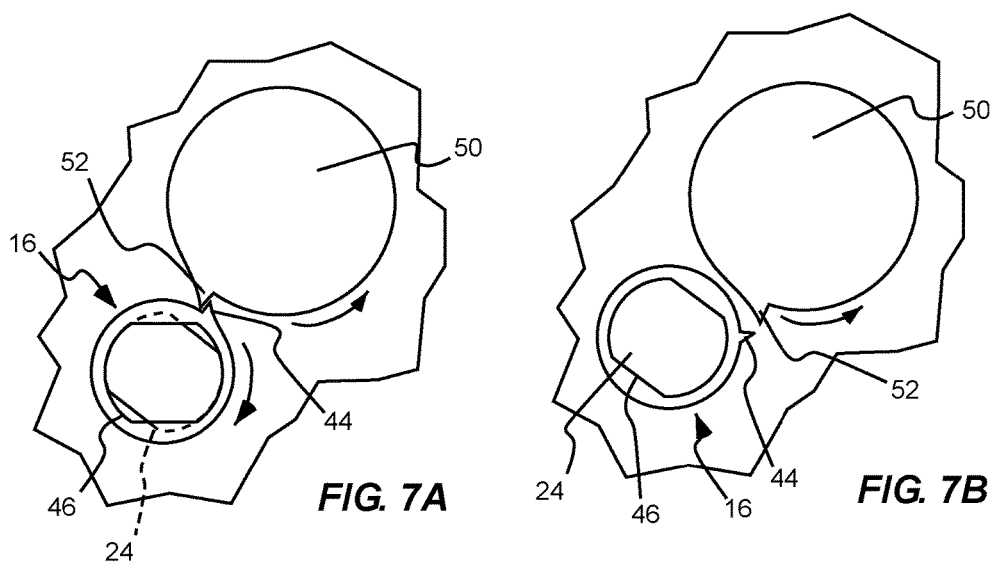
FIG. 6
FIG. 7A
FIG. 7B

SYSTEMS FOR DIFFUSING VOLATILE COMPOUNDS UTILIZING MOVEABLE PODS

BACKGROUND OF THE INVENTION

Field of the Invention

The present invention relates generally to systems for diffusing volatile compounds such as fragrant materials, disinfectants and pesticides into surround air.

Related Art

There exist a variety of systems that diffuse volatile compounds into an environment. One such example is the well-known air freshener that diffuses scented materials to freshen the air of homes, vehicles, offices and the like. Air fresheners such as these can be as simple as cardstock impregnated with a volatile compound, or as sophisticated as electronic systems that selectively diffuse measured quantities of liquefied compounds at varying frequency and potency.

While many such systems exist, they generally suffer from significant loss of performance over time, or they are so complex that cost considerations become prohibitive, or both. For at least these reasons, designers continue to seek solutions to simplify operation of such systems while maintaining superior performance.

SUMMARY OF THE INVENTION

In accordance with one aspect of the invention, a system for diffusing one or more volatile compounds included in a volatile compound mass is provided, the system including a base and a pod tray, carried by the base. At least one pod can be carried by the pod tray, the pod having a housing holding a volatile compound mass. The volatile compound mass and the housing are moveable relative to one another. Moving the housing and the volatile compound mass relative to one another exposes the volatile compound to surrounding air in the environment thereby allowing a volatile compound to be diffused into the surrounding air. An actuator can be carried by the base, the actuator operable to engage the pod and move the housing and the volatile compound mass relative to one another. The pod and the actuator can be positionable relative to one another such that the pod and the actuator can be positioned proximate to one another to enable the actuator to engage the pod and move the housing of the pod and the volatile compound mass relative to one another to thereby diffuse the volatile compound.

In accordance with another aspect of the invention, a system for diffusing one or more volatile compounds from a volatile compound mass is provided, the system including a base and a pod tray, carried by the base. A plurality of pods can be carried by the pod tray, the pods each having a housing holding a volatile compound mass and having a keyed opening formed therein. The volatile compound mass and the housing can be moveable relative to one another. A biasing element can be positioned below each pod, the biasing element carrying a keyed pad having a shape corresponding to the keyed opening formed in the pod housing. An actuator can be carried by the base, the actuator being positionable relative to the pods such that the actuator can selectively engage a housing of one of the pods, then rotate the housing of the pod to cause the keyed opening in the housing to align with the keyed pad carried by the biasing element, thereby allowing the biasing element to at least partially expel the volatile compound mass from the housing to thereby allow the volatile compound to be diffused.

In accordance with another aspect of the invention, a method is provided of diffusing a volatile compound included in a volatile compound mass within a housing of a pod, the housing of the pod including a keyed opening formed therein and being positioned over a biasing element carrying a keyed pad. The method can include positioning an actuator proximate to a pod, and rotating, with the actuator, one of the pod housing and the keyed pad relative to one another to thereby align the keyed pad with the keyed opening formed in the pod housing, thereby allowing the biasing element to expel the volatile compound mass from the pod housing to thereby allow the volatile compound included in the volatile compound mass to be diffused.

Additional features and advantages of the invention will be apparent from the detailed description which follows, taken in conjunction with the accompanying drawings, which together illustrate, by way of example, features of the invention.

BRIEF DESCRIPTION OF THE DRAWINGS

The following drawings illustrate exemplary embodiments for carrying out the invention. Like reference numerals refer to like parts in different views or embodiments of the present invention in the drawings.

FIG. 6 is a top view of the system of FIG. 1, with the pod tray and cover omitted for clarity;

FIG. 7A is a bottom view of an actuator gear engaging a diffusion pod in accordance with an embodiment of the invention; and FIG. 7B is a bottom view of the actuator gear and diffusion pod of FIG. 7A, after the actuator has rotated so as to no longer engage the pod.

DETAILED DESCRIPTION

Figure 1:
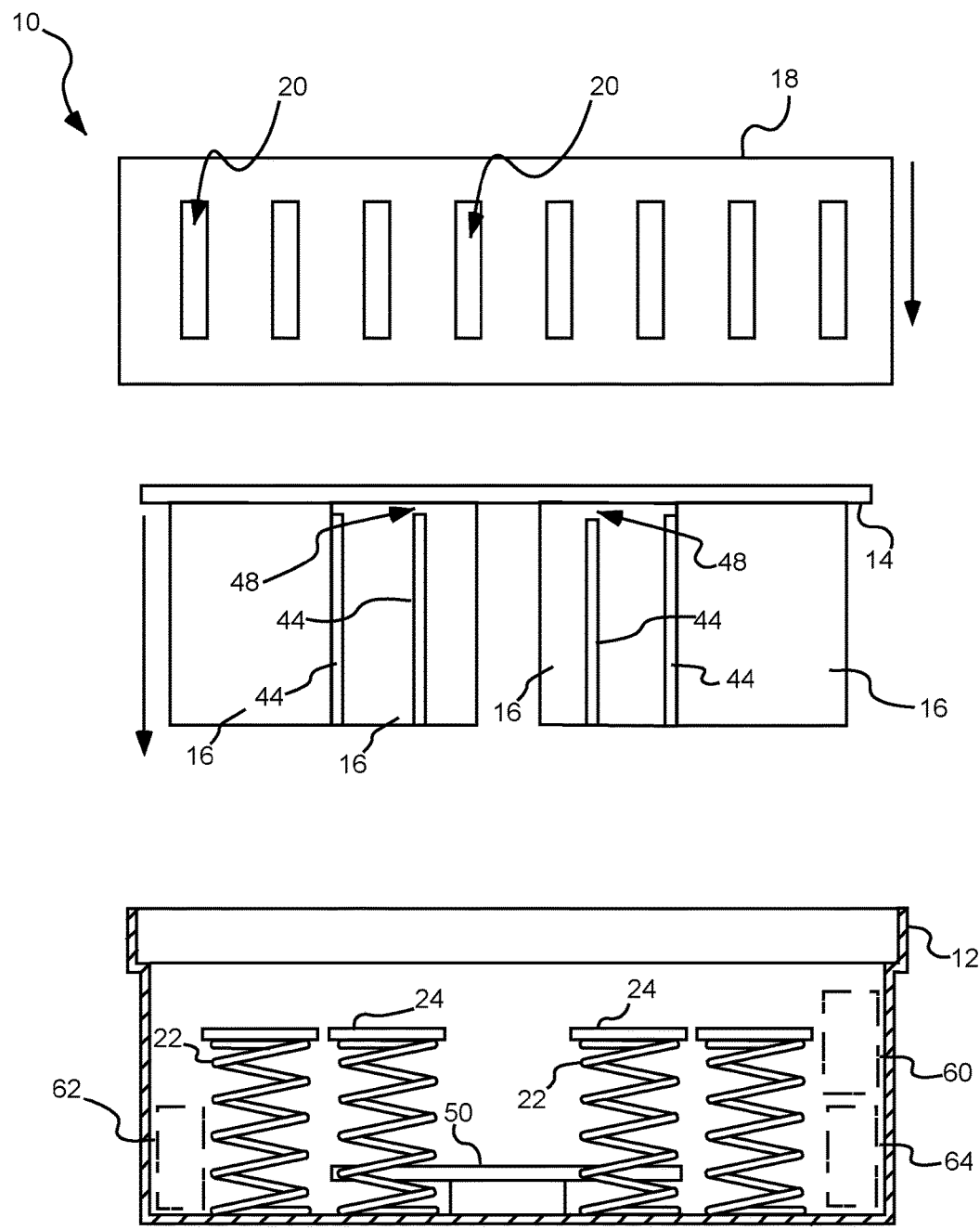
FIG. 1 is a side, partially exploded and partially sectioned view of a system for diffusing volatile compounds in accordance with an embodiment of the invention, the section of the base 12 taken along section 1-1 of FIG. 4.

Reference will now be made to the exemplary embodiments illustrated in the drawings, and specific language will be used herein to describe the same. It will nevertheless be understood that no limitation of the scope of the invention is thereby intended. Alterations and further modifications of the inventive features illustrated herein, and additional applications of the principles of the inventions as illustrated herein, which would occur to one skilled in the relevant art having possession of this disclosure, are to be considered within the scope of the invention.

Definitions

As used herein, the singular forms "a" and "the" can include plural referents unless the context clearly dictates otherwise. Thus, for example, reference to "a diffusion pod" can include one or more of such pods, if the context dictates.

As used herein, the term "substantially" refers to the complete or nearly complete extent or degree of an action, characteristic, property, state, structure, item, or result. As an arbitrary example, an object that is "substantially" enclosed is an article that is either completely enclosed or nearly completely enclosed. The exact allowable degree of deviation from absolute completeness may in some cases depend upon the specific context. However, generally speaking the nearness of completion will be so as to have the same overall result as if absolute and total completion were obtained. The use of "substantially" is equally applicable when used in a negative connotation to refer to the complete or near complete lack of an action, characteristic, property, state, structure, item, or result. As another arbitrary example, a composition that is "substantially free of" an ingredient or element may still actually contain such item so long as there is no measurable effect as a result thereof.

As used herein, the term "about" is used to provide flexibility to a numerical range endpoint by providing that a given value may be "a little above" or "a little below" the endpoint.

Relative directional terms are sometimes used herein to describe and claim various components of the diffusion systems of the present invention. Such terms include, without limitation, "upward," "downward," "horizontal," "vertical," etc. These terms are generally not intended to be limiting, but are used to most clearly describe and claim the various features of the invention.

Where such terms must carry some limitation, they are intended to be limited to usage commonly known and understood by those of ordinary skill in the art having possession of this disclosure. For example, directional terms can be used herein to refer to various aspects of the present volatile compound diffusion systems in the case where the diffusion systems are used as a tabletop application. One of ordinary skill in the art will appreciate that the present systems can be used in a variety of other orientations, such as wall-mounted units or ceiling-mounted units. In these cases, the directional terms will, of course, apply differently to the system. One of ordinary skill in the art having possession of this disclosure will readily appreciate the adaptability of such terms to varying orientations of the present technology.

As used herein, a plurality of items, structural elements, compositional elements, and/or materials may be presented in a common list for convenience. However, these lists should be construed as though each member of the list is individually identified as a separate and unique member. Thus, no individual member of such list should be construed as a de facto equivalent of any other member of the same list solely based on their presentation in a common group without indications to the contrary.

Numerical data may be expressed or presented herein in a range format. It is to be understood that such a range format is used merely for convenience and brevity and thus should be interpreted flexibly to include not only the numerical values explicitly recited as the limits of the range, but also to include all the individual numerical values or sub-ranges encompassed within that range as if each numerical value and sub-range is explicitly recited. As an illustration, a numerical range of "about 1 to about 5" should be interpreted to include not only the explicitly recited values of about 1 to about 5, but also include individual values and sub-ranges within the indicated range. Thus, included in this numerical range are individual values such as 2, 3, and 4 and sub-ranges such as from 1-3, from 2-4, and from 3-5, etc., as well as 1, 2, 3, 4, and 5, individually.

This same principle applies to ranges reciting only one numerical value as a minimum or a maximum. Furthermore, such an interpretation should apply regardless of the breadth of the range or the characteristics being described.

Invention

The present technology provides systems and methods for controllably releasing various volatile compounds into an environment. Such volatile compounds include, without limitation, fragrant materials, pesticides, repellants, disinfectants, etc. In the interest of clarity, much of the discussion below will focus on the use of the technology to deliver fragrant material, as an air freshener. It is, however, to be understood that the present invention is not limited to such applications and can be utilized in a variety of air treatment regimes in various environments.

Traditional air fresheners are well known and used by many people to treat the air in a home, vehicle, or place of business. One primary limitation of these traditional air fresheners is the loss of performance, either real or perceived, over time. Most delivery mechanisms exhibit a noticeable decay in the amount of fragrance that is being delivered over time. To compound this issue, most consumers will also begin to become anosmic to the fragrance after a short period of time, which limits the consumer's ability to appreciate the fragrance. This leads to the perception that air fresheners only last a short period of time, when in reality they may continue to deliver fragrance for much longer. Some devices have attempted to counter one or both of these issues by focusing on linear fragrance delivery, or by alternating between fragrances to address anosmia. However, these devices are very complicated and expensive, so there remains an unmet need for simple and low-cost devices that can address these issues.

The present technology provides a simple device that utilizes very little power to periodically activate a new fragrance on a selectable time interval with no interaction required from the user. This device enables the consumer to load a custom combination, or "playlist," of their favorite fragrances, which can then be activated over time to maintain a fresh fragrance experience by continuously changing the fragrance. The present systems use a very simple and efficient motion that enables the devices to use very little power and are accordingly very simple to operate.

FIG. 1 illustrates a partially exploded system 10 for diffusing a volatile compound. The system includes a base 12 and a pod tray 14 carried by the base. The pod tray can carry, via openings 40 (FIG. 4), a plurality of diffusion pods 16. A cover 18 can be provided that can include a series of openings 20 formed therein. Once assembled, the openings allow the volatile material, after it has diffused from the pods, to migrate from the system and enter the surrounding environment.

In operation, a series of diffusion pods 16 can be loaded through the pod tray 14 and into the base 12. Once the pods are loaded, the cover 18 can be placed atop the base to at least partially conceal the pods and pod tray. The pods can then be activated, as discussed in more detail below, at select times and/or durations to provide a simple but effective air freshener system.

Figure 2:
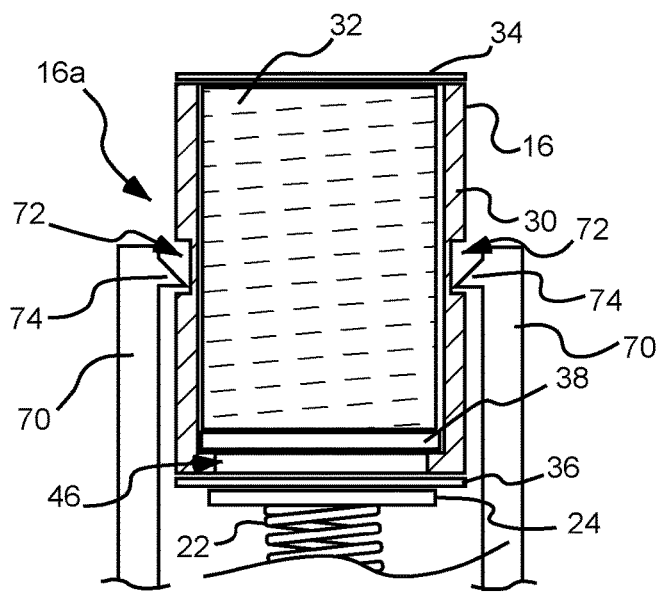
FIG. 2 is side, partially sectioned view of a diffusion pod and spring assembly in accordance with an embodiment of the invention.

A more detailed view of an exemplary pod 16a is shown FIG. 2. In this example, the pod can include an outer pod housing 30 which houses a volatile compound mass 32. The volatile compound mass is generally a quantity of material that includes one or more volatile compounds that are diffused upon exposure to the environment. An upper seal 34 and a lower seal 36 can contain the volatile compound within the outer pod housing 30 until it is desired to diffuse the volatile compound (e.g., to "activate" the pod).

Activation of the pods 16 is discussed in more detail below. Generally speaking, however, the term "activation" is used herein to describe a condition in which volatile compounds included in a volatile compound mass are allowed to diffuse into a surrounding environment. In the case of the pods shown in the figures, this typically involves moving some structure relative to another such that a volatile compound mass that was previously contained in a sealed closure is exposed to the surrounding environment. Exposure of the volatile compound mass results in diffusion of volatile compounds carried by the mass.

In the examples shown, activation can be achieved by forcing moveable base 38 upwardly, thereby at least partially expelling the volatile compound mass 32 from the housing 30 exposing the volatile compound mass to surrounding air. While not required, the upper and lower seals 34, 36 can be formed from a frangible material that is compromised as the moveable base is forced upward. Suitable examples of this material include, without limitation, thin metallic or polymeric materials, paper, card stock, gels or gel-like materials, etc. The one or more volatile compounds included in the volatile compound mass 32 are retained within the pod housing 30 while the seals 34 and 36 remain intact, and released once the seals are broken.

The volatile compound mass 32 can be formed from a variety of materials. Suitable compositions include, without limitation, scented aqueous gels, scented non-aqueous gels, waxes, permeable membranes, or fragrance-infused absorbent material such as paper, fibrous masses, ceramic, porous plastic, wood, or inorganic porous solids (i.e. salt), etc. Generally, exposure of the volatile compound mass to the environment results in one or more volatile compounds being released from the volatile compound mass into the environment to act as a fragrant agent, insecticide, pesticide, repellant, disinfectant, etc. In the examples shown in the present disclosure, the mass 32 is at least partially solid, so that it retains its shape independently of the structure containing the mass. In some embodiments the mass could include a liquid reservoir having volatile compounds therein and a structure including permeable membrane through which volatile compounds can pass thereby leaving the liquid reservoir and passing into the air of the surrounding environment.

During assembly of the device, each pod 16 is placed upon a biasing element or spring 22. A keyed pad 24 is generally carried by the spring, or is otherwise positioned between the spring and the housing 30. The keyed pad and the spring are compressed beneath the pod as the pod is inserted into and through the pod tray 14 (see the spring 22 in FIG. 2 in a compressed condition). This can be done by a consumer, who can be provided with a variety of pods from which he or she can choose, or it can be done at the time of manufacture. As will be discussed in more detail below, actuation of the spring results in forcing the volatile compound mass from the housing, which in turn results in diffusion of the volatile compound.

Retaining the housing 30 over the spring 22 when the spring is in a compressed condition can be accomplished in a variety of manners. FIG. 2 illustrates one embodiment in which pod 16a includes a variety of features discussed above and below, and also includes a pair of retaining prongs 70 that can extend upwardly from the base 12 and can engage a slot 72 formed in the housing of the pod. The retaining prongs can include a catch 74 that can "snap" into the slot and retain the housing 30 upon the compressed spring, while still allowing the housing to rotate relative to the prongs. In this manner, the housing is maintained in position even when the volatile compound mass 32 is forced by the spring upwardly relative to the housing.

The prongs 70, slot 72 and catch 74 are only illustrated in association with pod 16a in FIG. 2 and are only one example of suitable structure that can be used to retain the housing 30 within the base 12. It is to be understood that omission of some of these features from the other drawing views is in the interest of clarity, and does not limit or otherwise affect the technology shown in the remaining views. In addition to the structure shown, it is also contemplated that the housing 30 can be retained below the pod tray 14 by slightly rotating the housing after insertion of the pod, such that an upper portion of rib 44 contacts the undersurface of the pod tray.

Figure 4:
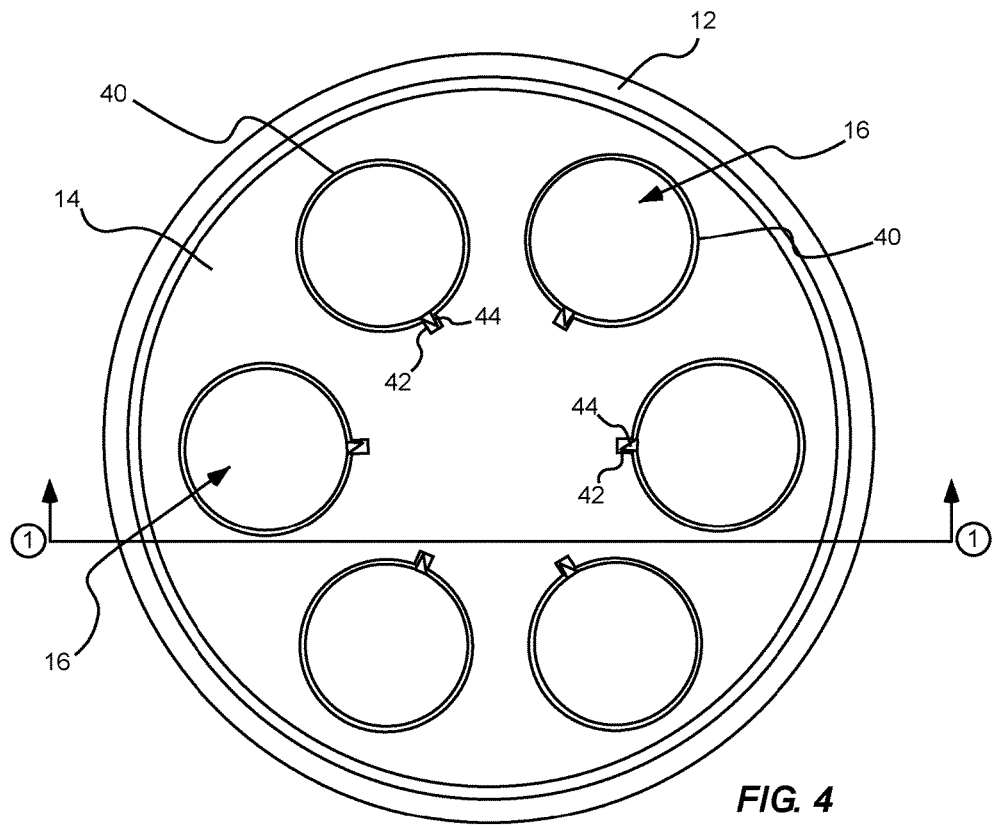
FIG. 4 is a top view of the system of FIG. 1, shown assembled with the cover omitted for clarity.
Figure 5A:
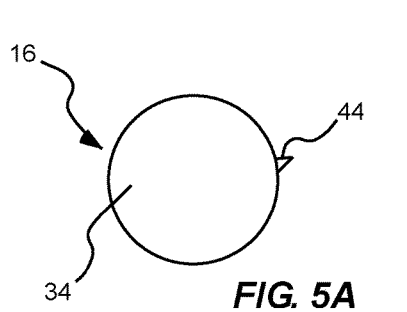
FIG. 5A is a top view of one of the diffusion pods of FIG. 1.
Figure 5B:
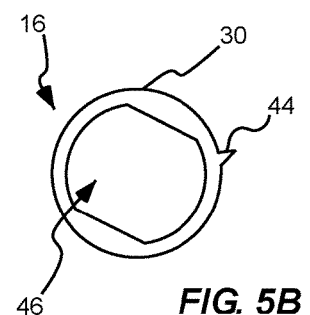
FIG. 5B is a bottom view of the diffusion pod of FIG. 5A.

FIG. 4 illustrates a series of pods 16 installed within the pod tray 14. The pod tray includes a series of openings 40 formed therein, one opening for each pod. Each opening can include a keyed extension 42 that can ensure that the pod is restricted to installation within the opening in a specific orientation. As shown in FIGS. 5A and 5B, each pod can include a rib 44 extending therefrom. In order for the pod to be installed into the opening formed in the pod tray, the rib must be aligned with the keyed extension in the opening. While the keyed extension is shown as a generally rectangular opening, a variety of shapes could be used, as long as the pod is restricted to a specific orientation.

Similarly, while the rib 44 is shown as generally triangular, a variety of shapes could also be used to accomplish the goal of indexing the pods in a particular orientation during assembly. As discussed in more detail below, however, the rib on the pod housing 30 also provides a mechanism by which the housing can be rotated. Thus, the rib can be sized and shaped and positioned to perform both of these functions. These functions can also be performed by different components: for example, a separate tooth (not shown) can be coupled to the pod housing, and this tooth can be engaged by the actuator to rotate the housing.

Each rib 44 can extend longitudinally along the housing. As shown in FIG. 1, the rib can terminate a short distance from an upper portion of the pod housing 30 in order to leave a gap 48. The gap ensures that the pod, once fully installed within the pod tray 14, can rotate within openings 40 (FIG. 4). Thus, the rib can ensure proper initial alignment, but does not interfere with rotation of the housing 30 after being fully inserted into opening 40.

Figure 3:
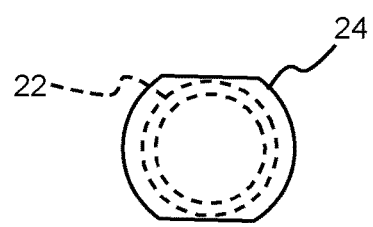
FIG. 3 is a top view of one of the springs of the system of FIG. 1.

FIGS. 5A and 5B provide more detailed views of a single pod 16. As shown in FIG. 5B, the pod housing includes a keyed opening 46 formed in a bottom surface thereof (note that bottom seal 36 is omitted from this view for clarity). This keyed opening is designed to correspond to the profile of the keyed pad 24 carried by the spring 22. A comparison of the top view of the keyed pad in FIG. 3 and the bottom view of the housing 30 with keyed opening 46 in FIG. 5B illustrates this relationship. Note that, while the profiles of the two are the same, the keyed pad is sized slightly smaller than the keyed opening, to allow the pad to enter the opening when properly aligned.

In the condition shown in FIG. 2, the keyed pad 24 is rotated relative to the keyed opening 46. In this state, the keyed pad will not pass into the keyed opening, and thus the spring 22 is prevented from expelling the volatile compound mass 32 from the pod housing 30. However, upon rotation of either the pod housing 30 (and thus the keyed opening formed therein) or the keyed pad, the profiles of the keyed pad and the keyed opening can align. At this point, the keyed pad will be able to enter the keyed opening, and the spring can force the volatile compound mass from the pod housing.

Thus, in the example shown, activation of the pod 16 (e.g., exposure of the volatile compound mass 32), is achieved by rotating the housing 30 of the pod until the keyed pad 24 and the keyed opening 46 are aligned, at which point the spring 22 at least partially forces the volatile compound mass from the housing. At this point, one or more volatile compounds included in the volatile compound mass can be diffused into the surround environment.

Rotation of the keyed pad 24 and the keyed opening 46 in the pod housing 30 relative to one another can be achieved in a variety of manners. FIGS. 6, 7A and 7B illustrate one exemplary way of accomplishing this. Note that these figures do not necessarily include all of the structure illustrated in other views: they are intended to illustrate, in the most straightforward manner, the operation of a select few components. Thus, for example, while FIGS. 7A and 7B are bottom views of a pod and an actuator, any structure that retains the pod and actuator in position (or moves the pod or actuator) is omitted for clarity.

In this example, six pods 16 are shown in FIG. 6 arranged about the base 12. Each pod includes a rib 44 that, as discussed above, is positioned in a particular orientation when the pods are installed. An actuator 50 is positioned amidst the pods. In this example, the actuator is rotatable about a central axis, as shown by directional indicator 56. The actuator can include an engagement tooth 52. As the actuator rotates, the engagement tooth engages the rib 44 of one of pods 16. Once engaged, the actuator continues to rotate and the housing 30 of the pod is caused to rotate. Rotation of the housing results in rotation of the keyed opening 46 formed in the housing.

This sequence of events is shown in more detail in FIGS. 7A and 7B. In FIG. 7A, engagement tooth 52 of actuator 50 has rotated to a position just prior to engaging rib 44. Thus, in this position, the keyed opening 46 and the keyed pad 24 are misaligned: the spring (not shown in this view) is thus prevented from expelling the volatile compound mass (not shown in this view) therefrom. However, as the pod housing, and thus the keyed opening, is rotated, it will align with the keyed pad, as shown in FIG. 7B. Once the keyed opening and the keyed pad are thus aligned, the keyed pad is forced by the spring through lower seal 36 (see FIG. 2), into and through the keyed opening and then engages and forces upward the moveable base 38. As the base 38 is forced upward, it forces the volatile compound mass upwardly and through upper seal 34. At this point, volatile compounds are diffused from the volatile compound mass and are allowed to exit the system through openings 20 formed in cover 18 (FIG. 1).

Rotation of the actuator 50 and pod tray 14 (and thus the pods 16) relative to one another can be performed in a variety of manners. In the example shown, actuator 50 can be rotationally coupled to the base 12 in a variety of known manners. As shown schematically in FIG. 1, the actuator can be rotated by way of a motor 60, which can be driven by a power source 62 and controlled by a regulator/controller 64. The motor can be any of a variety of available motors capable of producing the movement described.

The power source 62 can vary, as well. In one aspect of the invention, the system can be powered by mechanical power, delivered, for example, by a "wind-up" mechanism that stores energy in the form of springs and/or similar components. Such mechanisms are known for use in analogous applications, such as timepieces, animatronics, toys, etc. Alternately, a DC battery power source can be used, as can available AC household current.

The controller/regulator 64 can provide flexible functionality to the system. The controller can activate the motor for a particular duration and at a particular speed, until, for example, a particular pod is activated. After this period, the controller can pause the actuator to allow some or all of the volatile compounds in a pod to diffuse. After a suitable time, controller can then activate the motor again to move the system to activate an additional pod. A program to control such operation can be selected, for example, to activate a certain pod for one week, after which another pod could be activated for another week, etc. Any of a myriad of activation frequency and/or duration cycles can be achieved.

The power 62, control 64 and motor 60 functions can vary widely, as is best suited for any particular application. Due to this, these components are illustrated schematically in FIG. 1, without regard to their actual size, dimensions, relative placement, etc. While detailed examples of such systems are omitted from this disclosure, one of ordinary skill in the art having possession of this disclosure could readily adapt the current technology for use with any such power and control systems.

Activation of the pods (e.g., movement of the pod housing relative to the volatile compound mass) is shown herein by the use of a rotational actuator in connection with engagement structure formed on the pod housing. Thus, activation is accomplished through the use of motion of the pod housing relative to the volatile compound mass. It is to be understood, however that activation of the pods can be achieved in a variety of other manners. For example, one or more linear actuators can be used to move the volatile compound mass relative to the housing, or vice versa.

Also, while the examples shown actuate a single pod, in one embodiment the system can activate two or more pods simultaneously. For example, actuator 50 can include a second engagement tooth (not shown), which can activate a second pod during movement of the actuator relative to the pod tray.

In addition to the structural components discussed above, the present invention also provides various methods of diffusing volatile compounds carried by a pod, methods of installing diffusion pods within an activation system, and methods of treating or conditioning an environment with volatile compounds.

It is to be understood that the above-referenced arrangements are illustrative of the application for the principles of the present invention. Numerous modifications and alternative arrangements can be devised without departing from the spirit and scope of the present invention while the present invention has been shown in the drawings and described above in connection with the exemplary embodiments(s) of the invention. It will be apparent to those of ordinary skill in the art that numerous modifications can be made without departing from the principles and concepts of the invention as set forth in the examples.

We claim:

1. A system for diffusing one or more volatile compounds included in a volatile compound mass, the system comprising:
   a base;
   a pod tray, carried by the base;
   at least one pod carried by the pod tray, the pod having a housing holding a volatile compound mass, the volatile compound mass and the housing being moveable relative to one another, whereby moving the housing and the volatile compound mass relative to one another exposes a volatile compound to surrounding air; and an actuator, carried by the base, the actuator operable to engage the pod and move the housing and the volatile compound mass relative to one another;

the pod and the actuator being positionable relative to one another such that the pod and the actuator can be positioned proximate to one another to enable the actuator to engage the pod and move the housing of the pod and the volatile compound mass relative to one another to thereby diffuse the volatile compound.

2. The system of claim 1, wherein the pod tray is stationary relative to the base, and wherein the actuator moves relative to the pod tray.

3. The system of claim 1, wherein the actuator is rotatably moveable relative to the pod tray.

4. The system of claim 1, further comprising a biasing element positioned below the pod.

5. The system of claim 4, wherein the pod housing includes a keyed opening formed therein, and further comprising a keyed pad disposed between the biasing element and the housing, wherein the biasing element forces the volatile compound mass from the pod housing when the keyed opening and the keyed pad are aligned relative to one another.

6. The system of claim 5, wherein the pod housing is sealed by at least one cover, the cover being compromised as the biasing element forces the volatile compound mass from the pod housing.

7. The system of claim 1, further comprising a motor powered by an energy source, the motor operable to move the actuator relative to the pod tray.

8. The system of claim 7, wherein the energy source comprises a mechanical energy source.

9. The system of claim 7, wherein the energy source comprises an electrical energy source.

10. The system of claim 7, further comprising a regulator, operably coupled to the motor, the regulator operable to allow a user to control one of: activation frequency and activation duration of the at least one pod.

11. A system for diffusing one or more volatile compounds included in a volatile compound mass, the system comprising:
a base;
a pod tray, carried by the base;
a plurality of pods carried by the pod tray, the pods each having a housing holding a volatile compound mass and having a keyed opening formed therein, the volatile compound mass and the housing being moveable relative to one another;
a biasing element positioned below each pod, the biasing element carrying a keyed pad having a shape corresponding to the keyed opening formed in the pod housing;
an actuator, carried by the base, the actuator being positionable relative to the pods such that the actuator can selectively engage a housing of one of the pods, then rotate the housing of the pod to cause the keyed opening in the housing to align with the keyed pad carried by the biasing element, thereby allowing the biasing element to at least partially expel the volatile compound mass from the housing to thereby allow the volatile compound to be diffused.

12. The system of claim 11, wherein the housing is sealed by at least one cover, the cover being compromised as the biasing element forces the volatile compound mass from the housing.

13. The system of claim 11, further comprising a motor powered by an energy source, the motor operable to move the actuator relative to the pod tray.

14. The system of claim 13, wherein the energy source is one of: a mechanical energy source and an electrical energy source.

15. The system of claim 13, further comprising a regulator, operably coupled to the motor, the regulator operable to allow a user to control one of: activation frequency and activation duration of the pods.

16. A method of diffusing a volatile compound included in a volatile compound mass within a housing of a pod, the housing of the pod including a keyed opening formed therein and being positioned over a biasing element carrying a keyed pad, the method comprising:
positioning an actuator proximate to the pod; and
rotating, with the actuator, one of the pod housing and the keyed pad relative to one another to thereby align the keyed pad with the keyed opening formed in the pod housing, thereby allowing the biasing element to expel the volatile compound mass from the pod housing to allow the volatile compound included in a the volatile compound mass to be diffused.

17. The method of claim 16, wherein rotating one of the pod housing and the keyed pad comprises engaging the pod housing with a rotatable actuator and rotating the pod housing relative to the keyed pad.

18. The method of claim 17, wherein the rotatable actuator is rotated by a motor driven by an energy source.

19. The method of claim 18, wherein the energy source is one of a mechanical energy source and an electrical energy source.

20. The method of claim 18, wherein the energy source is controlled by a regulator, the regulator allowing a user to control one of: activation frequency and activation duration of the pod.

* * * * *